United States Patent [19]

Szabo

[11] Patent Number: 5,776,911
[45] Date of Patent: Jul. 7, 1998

[54] USE OF (S)-ADENOSYL-L-METHIONINE (SAME) AND ITS PHYSIOLOGICALLY TOLERATED SALTS FOR TREATING REPERFUSION DAMAGE CAUSED BY TEMPORARY FOCAL ISCHEMIA

[75] Inventor: Laszlo Szabo, Dossenheim, Germany

[73] Assignee: Knoll Aktiengesellscahft, Ludwigshafen, Germany

[21] Appl. No.: 776,006

[22] PCT Filed: Jul. 5, 1995

[86] PCT No.: PCT/EP95/02598

§ 371 Date: Jan. 16, 1997

§ 102(e) Date: Jan. 16, 1997

[87] PCT Pub. No.: WO96/02252

PCT Pub. Date: Feb. 1, 1996

[30] Foreign Application Priority Data

Jul. 16, 1994 [DE] Germany .......................... 44 25 280.3

[51] Int. Cl.⁶ .................................................. A61K 31/70
[52] U.S. Cl. ........................................................ 514/46
[58] Field of Search ..................................... 514/266, 46

[56] References Cited

FOREIGN PATENT DOCUMENTS

| 162 323 | 11/1985 | European Pat. Off. . |
| 424 543 | 5/1991 | European Pat. Off. . |
| 2 7293 | 2/1990 | Japan . |

OTHER PUBLICATIONS

Do MNDA Antagonists . . . Buchan, Cere. and Brain Metabolism Reviews, 1–25, 1990.

Sato et al. S–Adenosyl–L–Methionine . . . . 1151–1156, 1987, 39(12).

Background Review and Current Concept . . . . Hallenbeck et al., Neurological Review, vol. 47, Nov. 1990, 1245–1254.

Free Radicals and Their Involvement . . . Downey, Annu. Rev. Physiol, 1990 487–504.

Effect of S–adenosyl–L–Methionine . . . . European Jour., 1989, Yatsugi et al., 231–239.

Effects of S–Adenosyl–L–. . . Kozuka et al., Japan J. Pharm., 46, 225–236 1988.

A Phenothiazine Derivative Reduces . . . . Yu et al., Stroke, vol. 23, No. 9, Sep. 1992.

Effects of Antioxidants on the . . . Tasdemiroglu et al., Acta Neurochir, 1994, 131L 302–309.

The Molecular Basis . . . Ikeda et al., Neurosurgery, vol. 27, No. 1, 1990, 1–11.

Placebo–Controlled Trials . . . . Bilton et al., Acids Intern. Ltd. Drug Invest. 8(1) 1994, p. 10–20.

S–Adenosyl–L–Methionine . . . Matsui et al., Japan J. Pharm. 49, 119–124, 1989.

S–Adenosyl–L–methionine . . . . Matsui et al., European Journ. of Pharm., 144, 1987, 211–216.

AASLD Abstracts of Papers, Hepatology, 14 (4 Part 2) 1991.

Buchan et al., Brain Research, 574 (1992) 171–177.

Buchan et al., J. Neuroscience, 11(4), Apr. 1991, 1049–1056.

Ginsberg et al., Stroke, 20(12), Dec. 1989, 1627, 1628.

*Primary Examiner*—Phyllis G. Spivack
*Attorney, Agent, or Firm*—Keil & Weinkauf

[57] ABSTRACT

SAMe and its physiologically tolerated salts are administered to a patient for the treatment of reperfusion damage caused by temporary focal ischemia.

2 Claims, No Drawings

USE OF (S)-ADENOSYL-L-METHIONINE (SAME) AND ITS PHYSIOLOGICALLY TOLERATED SALTS FOR TREATING REPERFUSION DAMAGE CAUSED BY TEMPORARY FOCAL ISCHEMIA

This application is a 371 of PCT/EP95/02598 filed Jul. 5, 1995

(S)-Adenosyl-L-methionine (SAMe) and its salts have been disclosed, see EP-PS 162 323. The antiischemic effect of SAMe in principle has also been described (Eur. J. Pharmacol. 144 (1987) 211; Jpn. J. Pharmacol. 46 (1988) 225; Eur. J. Pharmacol. 166 (1989) 231; Jpn. J. Pharmacol. 52 (1990) 141). According to JP 8312642, SAMe can be used for various indications relating to central damage.

The antiischemic effect of SAMe has been shown, however, only in the treatment of global cerebral ischemia. Global cerebral ischemia arises from complete failure of the cerebral blood supply as occurs, for example, during cardiac arrest. It is known that the therapeutic effect of a substance on global ischemia is not applicable to other types of ischemic brain disorders, especially not to focal ischemias caused by occlusion of an intracranial vessel (Cerebrovasc. Brain Metab. Rev. Z (1990) 1).

It is furthermore known that restoration of the blood supply in cases of temporary focal ischemia induces secondary biochemical processes which lead to reperfusion damage (Arch. Neurol. 47 (1990) 1245). It is assumed that the reperfusion damage is primarily mediated by release of oxygen free radicals (superoxide and hydroxyl free radical) (Neurosurgery 27 (1990) 1). Although reperfusion is indispensable for preventing irreversible damage, in its turn it causes reperfusion damage. It is therefore possible to reduce further the extent of tissue damage by drugs if they minimize or prevent the reperfusion damage. These processes have been demonstrated both in the brain and in the heart (Ann. Rev. Physiol. 52 (1990) 487).

The principal types of temporary focal ischemia with which secondary damage of this nature may occur are the following: (1) acute thromboembolic ischemia, where reperfusion is initiated by administration of thrombolytic substances (such as urokinase, streptokinase or t-PA) or by surgical procedures, (2) vasospasms induced spontaneously or after administration of vasodilator substances, (3) surgical interventions in which temporary occlusion of an artery is initiated for surgical reasons, and (4) transient ischemic attacks of unexplained etiology. There is at present no accepted therapy for the treatment of reperfusion damage occuring as concomitant phenomenon of temporary focal ischemia.

The present invention relates to the use of SAMe and its physiologically tolerated salts for treating reperfusion damage induced by temporary focal ischemia.

SAMe is preferably employed in the form of a salt with a physiologically tolerated acid. Preferred acids are: hydrochloric acid, sulfuric acid, phosphoric acid, formic acid, acetic acid, citric acid, tartaric acid, methanesulfonic acid, p-toluenesulfonic acid and butanedisulfonic acid.

SAMe and its salts are administered for these indications in an amount of from 10 to 1,000 mg/kg of body weight.

SAMe can be administered parenterally (intravenously, intraarterially or intramuscularly) in a conventional way, and intravenous infusion is the preferred mode of administration. The abovementioned amount is, as a rule, infused into the patient once over a period of from 1 to 24 hours.

SAMe can be used in conventional liquid pharmaceutical forms, eg. as solution. The administration forms normally contain the active ingredient in an amount of from 1 to 50%, preferably 5 to 20%.

The particular advantage of the use of SAMe by comparison with other therapies is that the treatment with SAMe also shows an excellent protective effect even if it is initiated only in the reperfusion phase.

The efficacy of SAMe for reperfusion damage is shown by the following experiment taking the brain as example:

The effect of SAMe on the size of the cerebral infarct induced by temporary focal cerebral ischemia was investigated in the rat by a modification of the method of Chen et al. (Stroke 17 (1986) 738). For this purpose, under halothane-anasthesia, the right middle cerebral artery and the two common carotid arteries were exposed and occluded for 90 min. The size of the cerebral infarct was determined quantitatively 24 h later after staining with triphenyltetrazolium chloride.

The experimental animals in the substance group were treated intravenously with 40 mg/kg+100 mg/kg/h SAMe. The bolus dose was given either at the end of the 90-minute occlusion or 30 min later; infusion was maintained continuously for 6 h. As is evident from Table 1, the temporary vascular occlusion led to significantly smaller cerebral infarcts on treatment with SAMe than with placebo treatment (0.9% NaCl solution).

These findings clearly show the specific effect of SAMe on reperfusion processes: although therapy with SAMe was not initiated until the postischemic reperfusion phase, it caused a significant reduction in the resulting cerebral infarct.

TABLE 1

| Postischemic latency, min | | 0 | 30 |
|---|---|---|---|
| Infarct volume as % of the control (mean ± standard error [number of tests]) | Placebo | 100 ± 6 [7] | 100 ± 8 [11] |
|  | SAMe | 57 ± 6 [8] | 66 ±6 [10] |
| p (two-sided t test) | | <0.001 | <0.01 |

We claim:

1. A method of treating a patient suffering from reperfusion damage caused by temporary focal ischemia, which comprises administering to the patient an effective amount of (S)-adenosyl-L-methionine (SAMe) or a physiologically tolerated salt thereof.

2. The method of claim 1, wherein the acid is selected from the group consisting of hydrochloric acid, sulfuric acid, phosphoric acid, formic acid, acetic acid, citric acid, tartaric acid, methanesulfonic acid, p-toluenesulfonic acid and butanedisulfonic acid.

* * * * *